US010709390B2

United States Patent
Qian et al.

(10) Patent No.: US 10,709,390 B2
(45) Date of Patent: Jul. 14, 2020

(54) DEEP LEARNING ALGORITHMS FOR HEARTBEATS DETECTION

(71) Applicant: Logos Care, Inc., Mountain View, CA (US)

(72) Inventors: Kaizhi Qian, Champaign, IL (US); Yang Zhang, Urbana, IL (US); Thomas Y. Lo, Fremont, CA (US)

(73) Assignee: LOGOS CARE, INC., San Mateo, CA (US)

( * ) Notice: Subject to any disclaimer, the term of this patent is extended or adjusted under 35 U.S.C. 154(b) by 285 days.

(21) Appl. No.: 15/819,763

(22) Filed: Nov. 21, 2017

(65) Prior Publication Data

US 2018/0249964 A1 Sep. 6, 2018

Related U.S. Application Data

(60) Provisional application No. 62/466,288, filed on Mar. 2, 2017.

(51) Int. Cl.
*A61B 5/00* (2006.01)
*A61B 5/0404* (2006.01)
(Continued)

(52) U.S. Cl.
CPC .......... *A61B 5/7267* (2013.01); *A61B 5/0245* (2013.01); *A61B 5/0255* (2013.01); *A61B 5/02416* (2013.01); *A61B 5/02438* (2013.01); *A61B 5/02444* (2013.01); *A61B 5/0404* (2013.01); *A61B 5/04011* (2013.01);
(Continued)

(58) Field of Classification Search
CPC ....... A61B 5/02; A61B 5/024; A61B 5/02405; A61B 5/02438; A61B 5/7267
See application file for complete search history.

(56) References Cited

U.S. PATENT DOCUMENTS 5,749,366 A 5/1998 Odagiri et al.
5,957,855 A 9/1999 Oriol et al.
(Continued)

FOREIGN PATENT DOCUMENTS

WO WO 2015131065 A1 9/2015
WO WO 2016063795 A1 4/2016
WO WO 2016/145379 A1 9/2016

OTHER PUBLICATIONS

Begley, R.J. et al., "Adding Intelligence to Medical Devices", MDDI Medical Device and Diagnostic Industry News Products and Suppliers, Mar. 1, 2000, 6 pages, [Online] [Retrieved on Mar. 6, 2018] Retrieved from the Internet<URL:http://www.mddionline.com/article/adding-intelligence-medical-devices>.

(Continued)

*Primary Examiner* — Alyssa M Alter
(74) *Attorney, Agent, or Firm* — Fenwick & West LLP

(57) ABSTRACT

A system that detects heartbeats includes a sensor or a transducer and algorithms based on deep learning. The algorithms employ techniques of artificial intelligence that enable the system to extract heartbeat features under low signal-to-noise-ratio (SNR) conditions when a user is exercising. The algorithms can be applied to various technologies for heart rate monitoring such as ultrasound Doppler, photoplethysmogram (PPG), electrocardiogram (EKG), acoustic, pressure/force sensing and laser/RF Doppler, among other types of sensing methods.

25 Claims, 12 Drawing Sheets

(51) Int. Cl.
   *A61B 5/0245* (2006.01)
   *A61B 5/04* (2006.01)
   *A61B 5/024* (2006.01)
   *A61B 8/02* (2006.01)
   *A61B 5/0255* (2006.01)
   *A61B 8/08* (2006.01)
   *A61B 8/06* (2006.01)

(52) U.S. Cl.
   CPC .......... *A61B 5/7207* (2013.01); *A61B 5/7235* (2013.01); *A61B 5/7278* (2013.01); *A61B 8/02* (2013.01); *A61B 8/06* (2013.01); *A61B 8/488* (2013.01); *A61B 5/02405* (2013.01); *A61B 5/6823* (2013.01); *A61B 5/6831* (2013.01); *A61B 5/7257* (2013.01); *A61B 2503/10* (2013.01)

(56) References Cited

U.S. PATENT DOCUMENTS

| | | |
|---|---|---|
| 7,890,443 B2 | 2/2011 | Zhang et al. |
| 8,046,058 B2 | 10/2011 | Lin et al. |
| 8,234,228 B2 | 7/2012 | Weston et al. |
| 8,323,188 B2 | 12/2012 | Tran |
| 8,727,991 B2 | 5/2014 | Hasegawa-Johnson |
| 8,888,701 B2 | 11/2014 | Leboeuf et al. |
| 8,945,017 B2 | 2/2015 | Venkatraman et al. |
| 8,956,303 B2 | 2/2015 | Hong et al. |
| 8,990,126 B1 | 3/2015 | Bangalore et al. |
| 8,998,815 B2 | 4/2015 | Venkatraman et al. |
| 9,031,844 B2 | 5/2015 | Yu et al. |
| 9,039,614 B2 | 5/2015 | Yuen et al. |
| 9,113,795 B2 | 8/2015 | Hong et al. |
| 9,189,742 B2 | 11/2015 | London |
| 9,314,181 B2 | 4/2016 | Brockway et al. |
| 9,323,747 B2 | 4/2016 | Anisimovich et al. |
| 9,456,742 B2 | 10/2016 | Muto |
| 9,456,787 B2 | 10/2016 | Venkatraman et al. |
| 9,468,386 B2 | 10/2016 | Lopez et al. |
| 2005/0143668 A1 | 6/2005 | Lu et al. |
| 2006/0200036 A1* | 9/2006 | Kurzweil ............ A61B 5/046 600/518 |
| 2009/0043216 A1* | 2/2009 | Lin ..................... A61B 5/0205 600/501 |
| 2009/0227853 A1 | 9/2009 | Wijesiriwardana |
| 2011/0022199 A1* | 1/2011 | Paalasmaa ............ A61B 5/024 700/89 |
| 2011/0077484 A1 | 3/2011 | Van Slyke et al. |
| 2012/0016443 A1* | 1/2012 | Holmberg .......... A61N 1/36036 607/57 |
| 2014/0288390 A1* | 9/2014 | Hong ................ A61B 5/02427 600/301 |
| 2014/0142929 A1 | 10/2014 | Seide et al. |
| 2015/0031965 A1 | 1/2015 | Visvanathan et al. |
| 2015/0139536 A1 | 5/2015 | Jin et al. |
| 2015/0324690 A1 | 11/2015 | Chilimbi et al. |
| 2016/0106326 A1 | 4/2016 | Bajaj et al. |
| 2016/0140438 A1 | 5/2016 | Yang et al. |
| 2016/0151023 A1 | 6/2016 | Pamula |
| 2016/0284346 A1 | 9/2016 | Visser et al. |
| 2018/0082172 A1* | 3/2018 | Patel .................... G06N 3/0472 |

OTHER PUBLICATIONS

Alqaraawi, A. et al., "Heart Rate Variability Estimation in Photophlethysmography Signals Using Bayesian Learning Approach", Healthcare Technology Letters, 2016, pp. 136-142, vol. 3, Iss. 2.

Xu, K., et al. "Show, Attend and Tell: Neural Image Caption Generation with Visual Attention," arXiv preprint arXiv:1502.03044 2.3, Cornell University Library, 2015, 1 page, vol. 5, [Online] [Retrieved on Mar. 6, 2018] Retrieved from the Internet<URL:https://arxiv.org/abs/1502.03044>.

Dong, C., et al. "Learning a Deep Convolutional Network for Image Super-Resolution," European Conference on Computer Vision. Springer International Publishing, 2014, 16 pages.

PCT International Preliminary Report on Patentability Chapter II, PCT Application No. PCT/US2017/065467, dated Sep. 24, 2019, 11 pages.

PCT International Search Report and Written Opinion, PCT Application No. PCT/US17/65467, dated Mar. 7, 2018, 17 pages.

European Patent Office, Extended European Search Report and Opinion, EP Patent Application No. 17898936.4, dated Feb. 24, 2020, eight pages.

Shashikumar, S. P. et al., "A deep learning approach to monitoring and detecting atrial fibrillation using wearable technology," 2017 IEEE EMBS International Conference on Biomedical & Health Informatics (BHI), Feb. 2017, pp. 141-144.

* cited by examiner

DEEP LEARNING ALGORITHMS FOR HEARTBEATS DETECTION

CROSS REFERENCE TO RELATED APPLICATION

This application claims the benefit of priority under 35 USC § 119(e) to U.S. Provisional Application No. 62/466,288, filed on Mar. 2, 2017, which is incorporated herein in its entirety for all purposes.

BACKGROUND

1. Field of Art

This disclosure generally relates to a sensor system for detecting heartbeats and to signal processing to identify heartbeats from noisy sensor data.

2. Description of the Related Art

Heart rate tracking has become a function in many of today's mobile health monitoring devices. However, existing technologies are unable to accurately measure heart rate when subjects are jogging or running. The muscle artifacts compromise the signal-to-noise-ratio (SNR) that makes heartbeat detection difficult. Swimming, rowing, and weight lifting present even tougher challenges, for example, also due to low corresponding SNR.

An existing system for monitoring heart rate is based on electrocardiograms (EKG or ECG). The user is required to wear a chest strap and a wristwatch to display heart rate in real time. The electrodes on the chest strap pick up QRS waves (i.e., particular graphical features that may be shown on the EKG) as heartbeats. Heart rate can be computed based on the heartbeats. However, this system requires at least two separate hardware devices (chest strap and wrist watch), and wearing a chest strap is not particularly user friendly. Additionally, motion in the upper body may cause the electrodes to miss heartbeats frequently.

Other devices and methods to monitor heart rate without chest straps may use optical means to detect blood flow from the user's wrist. Photoplethysmography (PPG) is a general term of this approach that is usually applied to fingertips, earlobes, or wrist. PPG uses one or more light-emitting diodes (LED) with different wavelengths and one or more photodetectors. The LEDs shine light to the capillary arteries or arterioles underneath the skin. The reflected light sensed by the photodetectors changes in intensity, due to absorption of light by the red blood cells, at the same rate of the pulsating blood flow that is equivalent to heart rate. This approach may be simpler and easier to use than a chest strap. However, variations in skin pigmentation, ambient light, and outdoor climate conditions can limit the sensitivity and the dynamic range of the device because these variations may result in a low signal-to-noise-ratio (SNR). Further, digital signal processing (DSP) employed in such devices thus may require additional signals from motion sensors such as a multi-axis accelerometer to identify the rhythmic muscle motion in exercise.

SUMMARY

In an embodiment, a method for determining a heart rate of a subject includes obtaining temporal sensor data generated by a sensor worn by the subject (also referred to herein as a user), where the temporal sensor data represented by frames of data samples. The method further includes generating, for each of the frames, a feature vector based on a frequency domain representation of the corresponding data samples of the frame. The method further includes inputting the feature vectors to a model to generate a series of heartbeat determinations of the subject for each of the frames. The model includes a first set of parameters and associated weights that represent likelihoods of heartbeats of the subject as a function of time. The method further includes providing the heart rate of the subject determined based on the series of heartbeat determinations.

In some embodiments, the method further includes inputting the feature vectors to a scenario classifier to determine one of multiple scenarios for the temporal sensor data. The scenario classifier includes a second set of parameters and associated weights that represent likelihoods of the temporal sensor data corresponding to each of scenarios. The method further includes identifying the model from a set of trained models based on the determined scenario. In some embodiments, the method further includes identifying from the series of heartbeat determinations, one or more transitions between the stages of the plurality of heartbeat stages. Additionally, the method includes determining the heart rate of the subject based at least in part on a duration in time of the one or more transitions.

In another embodiment, a non-transitory computer-readable storage medium stores instructions that when executed by a processor causes the processor to execute the above-described method.

In yet another embodiment, a computer system includes a sensor, processor, and a non-transitory computer-readable storage medium that stores instructions for executing the above-described method. The sensor may be configured to be worn by a subject and generated temporal sensor data represented by frames of data samples.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The following description discloses systems and methods for using deep learning to extract vital sign signals from sensor data having low SNR or low signal energy to begin with. These techniques can be used for blood flow/heart rate monitoring using, ultrasound Doppler technology, PPG, among other types of sensors technologies. These techniques may outperform conventional EKG and PPG devices for heart rate determination in accuracy and user experience especially under heavy thumping conditions (e.g., noisy sensor data). In some embodiments, a wristband detects blood flow signals by either ultrasound or PPG to compute heart rate, without requiring a separate chest strap.

The techniques described herein can detect heartbeats and calculate heart rate accurately in low SNR situations. Other applications of continuous heart rate monitoring include Atrial Fibrillation (AF) detection and Heart Rate Variability (HRV) monitoring. Deep learning techniques may be employed for accuracy and reliability regardless of using EKG, PPG, or ultrasound.

Figure 1:
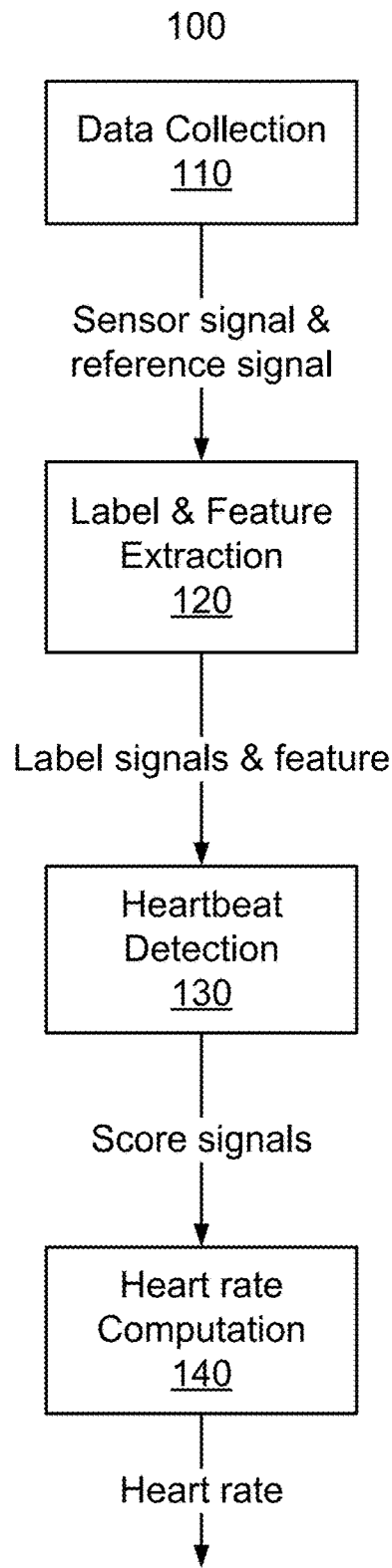
FIG. 1 is a flowchart of a method for determining heart rate according to one embodiment.

FIG. 1 is a flowchart of a method 100 for determining heart rate according to one embodiment. In one embodiment, a heart rate system (also referred to herein as a "system") performs steps of the method 100, for example, including algorithms or steps for data collection, label and feature extraction, heartbeat detection, and heart rate computation. In the data collection step 110, the heart rate system collects a sensor signal and reference signal using ultrasonic sensors, acoustic sensors, optical/PPG sensors, electrodes/EKG or pressure/force sensors and transducers, or other suitable types of sensors. Additionally, the heart rate system may collect a reference signal from a known reliable source, e.g., an EKG chest strap heart rate monitor, to guide the training of a classifier (also referred to herein as a model). In the label and feature extraction step 120, the heart rate system preprocesses the sensor signal and the reference signal to output a spectrogram feature and label signals. In the heartbeat detection step 130, the heart rate system detects the timestamps of heartbeats from the sensor signal. In the heart rate computation step 140, the heart rate system calculates heart rate based on the timestamps. The heart rate detection algorithms disclosed herein may be applied to any of the above-mentioned sensing technologies.

The method 100 may include different or additional steps than those described in conjunction with FIG. 1 in some embodiments or perform steps in different orders than the order described in conjunction with FIG. 1. Steps of the method 100 are further described below, with reference to the other figures as well.

I. DATA COLLECTION

Figure 10:
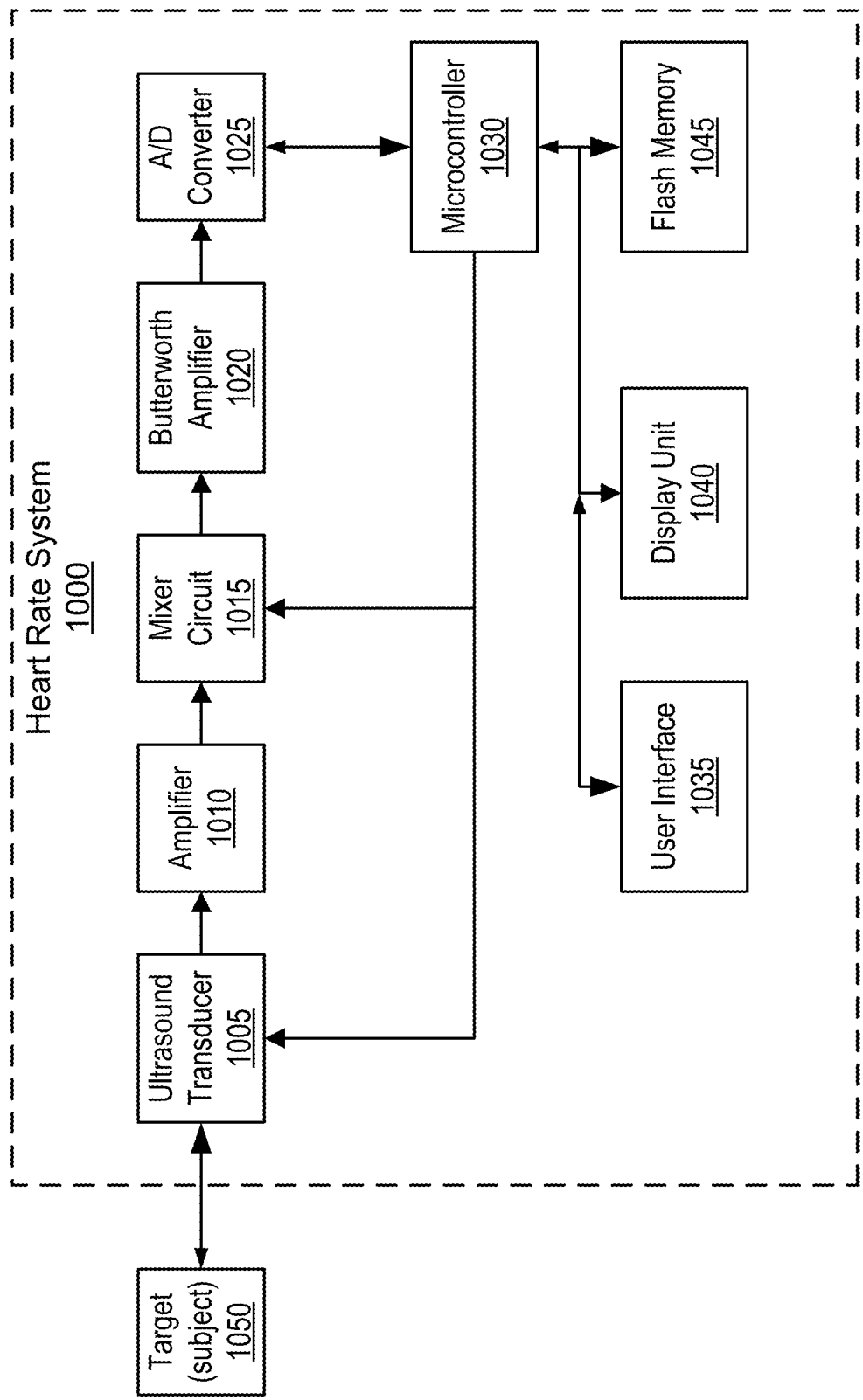
FIG. 10 is a block diagram of a heart rate system using ultrasound sensors according to one embodiment.
Figure 11:
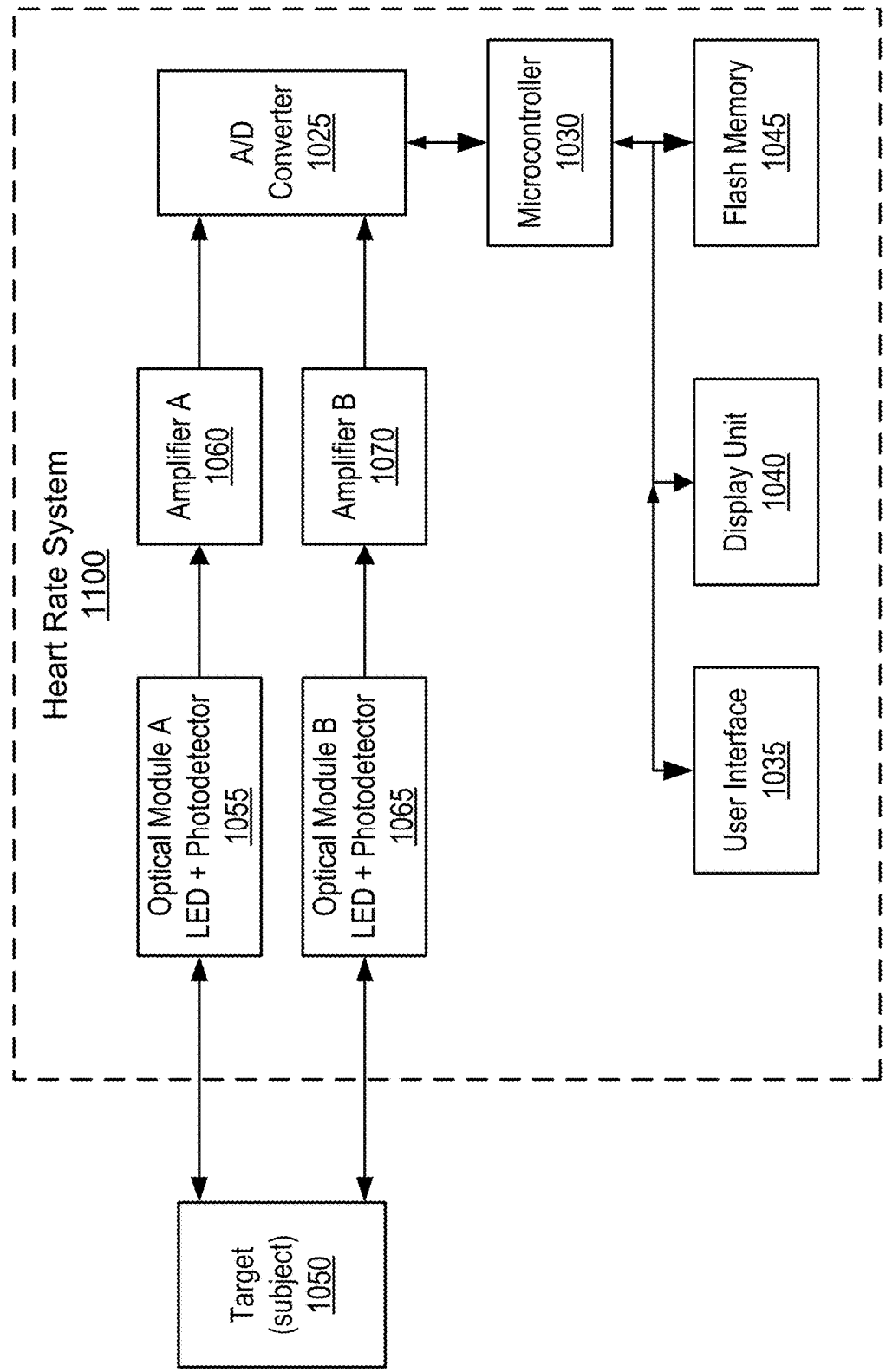
FIG. 11 is a block diagram of a heart rate system including optical sensors according to one embodiment.

In the data collection step 110, the heart rate system may acquire sensor signals (or sensor data) from an ultrasound transducer coupled to an amplifier and a mixer circuit (e.g., as shown in FIG. 10), in one embodiment. The ultrasound generator can output signals at frequencies between 1 to 10 megahertz (MHz). The output Doppler signal in audio range is sampled at 100 Hz to 10 KHz. In one use case, the output signals are at 5 MHz and the sampling rate is 4000 Hz. In another embodiment, the sensor data is acquired by an optical module (e.g., as shown in FIG. 11) including a light-emitting diode and a photo sensor followed by an amplifier. The output signal may be sampled at 100 Hz to 1 KHz. In one use case, the sampling rate is 500 Hz. The heart rate system may collect data for various scenarios, for example, no exercise (standing still), moderate exercise (slow and fast walking) and hard exercise (jogging and running), which may represent data with high SNR, moderate SNR, and low SNR, respectively.

In some embodiments, to build an artificial intelligence (AI) classifier that detects heartbeat features with precision, the heart rate system trains a classifier with a known reliable reference signal to identify the onset of each heartbeat in addition to the heartbeat signals itself. This reference signal is used in the training of the classifier. The reference signal may be provided by a chest strap including electrodes that detect the QRS wave of the subject's EKG. The chest strap may generate a narrow pulse signal for each heartbeat. The rising edge of the pulse can be used to mark the onset of a heartbeat.

II. LABEL AND FEATURE EXTRACTION

In the label and feature extraction step 120, the heart rate system may determine features using collected or processed sensor signals and/or other inputs to the heart rate system, e.g., a classifier. In an embodiment, the heart rate system derives label signals from the reference signals, and uses the label signals to guide the training of the classifier.

II. A. Feature Extraction

The heart rate system processes and obtains features from the sensor signal. In one embodiment, the sensor signal is framed with frame length $L_F$ (samples per frame) and frame rate $R_F$ (frames per second). $L_F$ may be any positive integer less than $F_S$, where $F_S$ is the sampling rate of the sensor signal. An example value of $L_F$ may be 256. $R_F$ may be any positive number greater than $F_S/L_F$. An example value of $R_F$ may be 10. In some embodiments, the heart rate system transforms each frame into a frequency representation using short-time Fourier transform (STFT), or other signal processing techniques. The frequency representation for each frame is a vector of length $L_F$. The heart rate system may truncate the frequency representation vectors, and retain a portion of the vectors with dimension 1 to dimension $L_F/2+1$. The heart rate system may remove or not process data in the other dimensions of the vector, e.g., including redundant information. The vector with retained dimensions is referred to as the feature vector for that frame.

Figure 2:
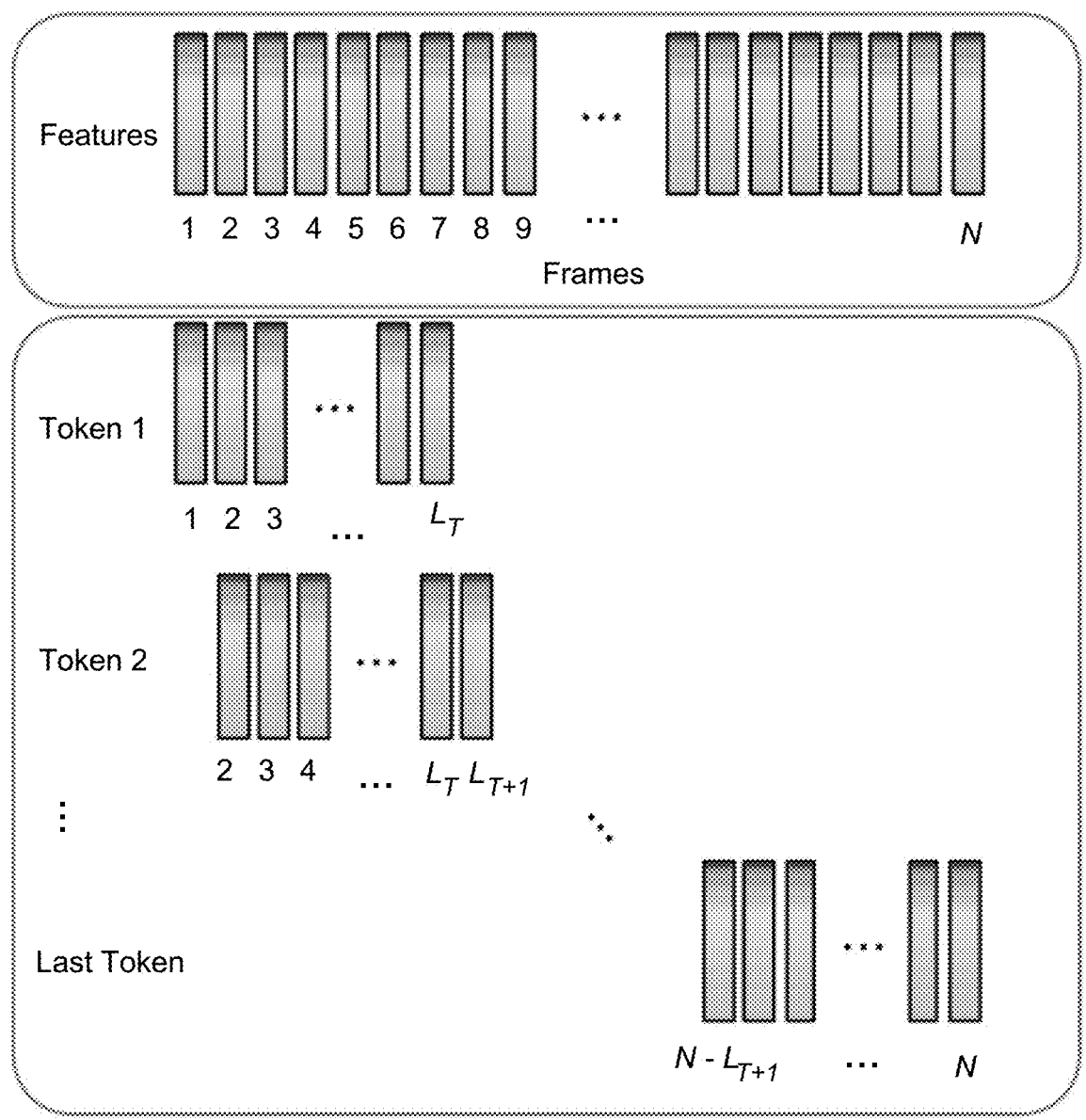
FIG. 2 is a diagram of features for determining heart rate according to one embodiment.

FIG. 2 is a diagram of features for determining heart rate according to one embodiment. In an embodiment, the heart rate system facilitates training by grouping feature vectors for frames into training tokens on a sliding window basis. As an example, a training token is a sequence of feature vectors of $L_T$ consecutive frames. $L_T$ may be any positive integer, and an example value may be 150. The frame range of the proceeding training token shifts from that of the current token by a predetermined value, e.g., one. FIG. 2 illustrates how feature vectors may be grouped into training tokens, which may help prevent the vanishing gradient problem or exploding gradient problem when training classifiers.

II. B. Label Extraction

Figure 3:
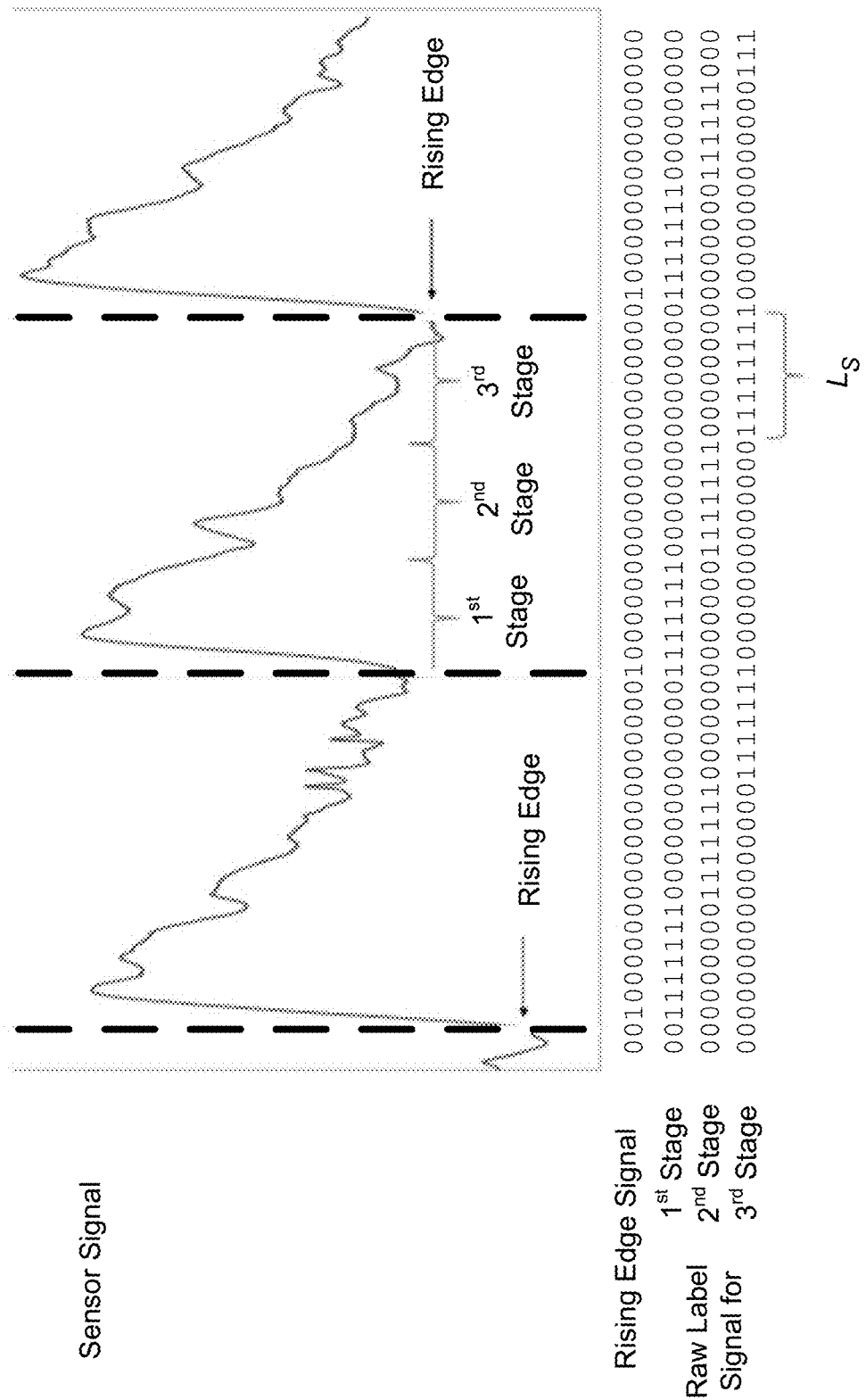
FIG. 3 is a diagram illustrating label extraction from a sensor signal according to one embodiment.

FIG. 3 is a diagram illustrating label extraction from a sensor signal according to one embodiment. The heart rate system may derive the label signals using a reference signal. In one embodiment, a system performs a label extraction process in steps as described below.

A reference signal includes, e.g., samples of 0's and 1's over time, where a 0 and 1 indicate no presence or presence of a heartbeat at a given timestamp, respectively. The heart rate system constructs the rising edge signal, which equals 1 at samples where the reference signal transitions from 0 to 1 (e.g., indicted by the dotted lines in FIG. 3), and equals 0 otherwise. These rising edges mark the determined onset of the heartbeats. FIG. 3 shows an example rising edge signal, as well as the amplitude (e.g., in millivolts) for an example sensor signal over time.

In some embodiments, the heart rate system divides each individual heartbeat cycle into N stages. N may be any positive integer, and an example value of N may be 3. Each stage is of length Ls (in number of samples), and an example value of Ls may be 250. The first stage starts at the rising edge and marks the start of a heartbeat cycle. Subsequent stages represent the later stages of the heartbeat cycle. An example is shown FIG. 3 with N=3, but N can be any positive integer. The heart rate system constructs raw label signals (also referred to as assigning labels to the training data). For each of the N stages, there is a corresponding raw label signal. Thus, there are a total of N raw label signals. Each raw label signal may include consecutive 1's within the corresponding stage and 0's otherwise. FIG. 3 shows examples of raw label signals for three stages.

Figure 4:
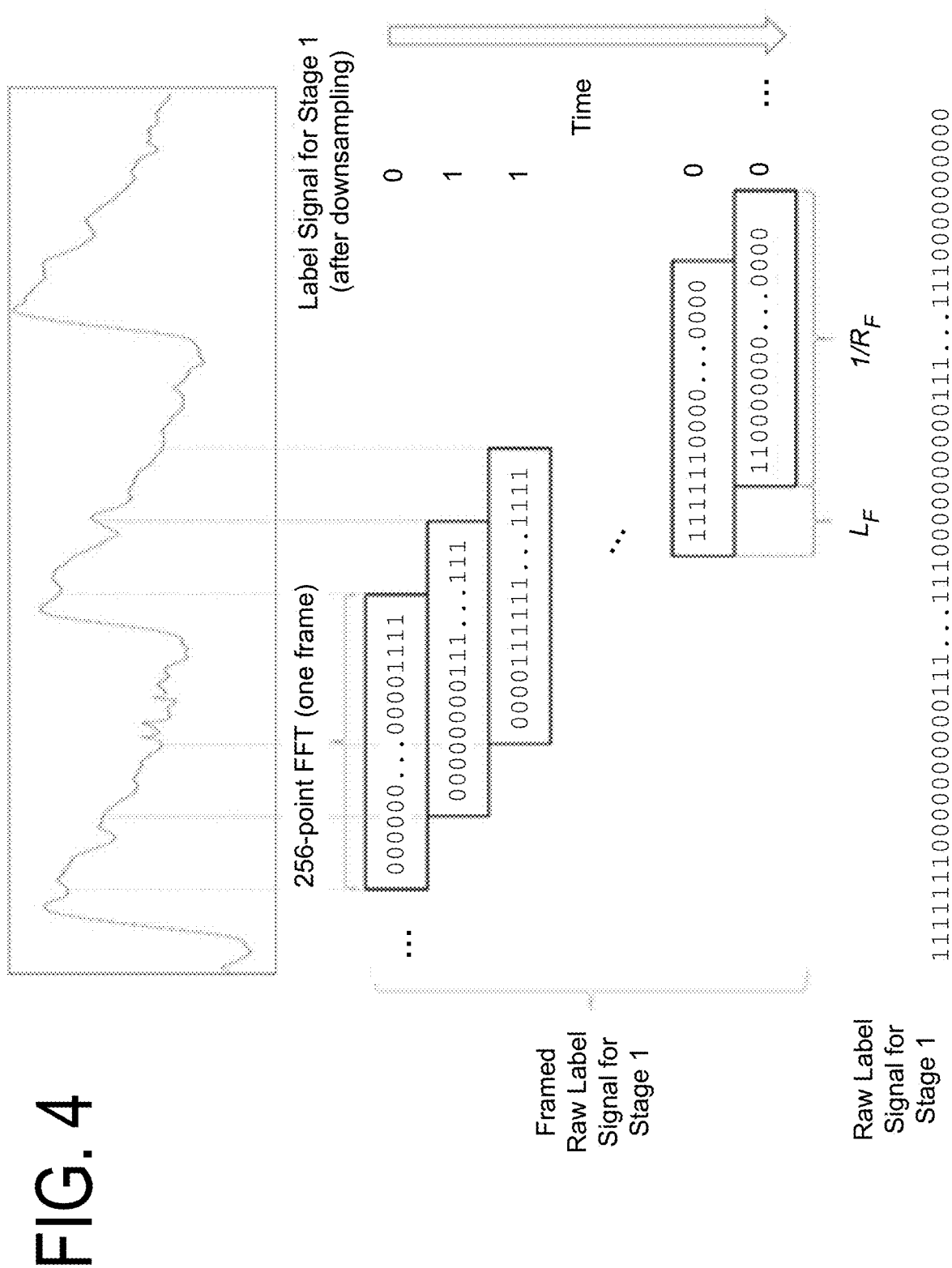
FIG. 4 is another diagram illustrating label extraction from a sensor signal according to one embodiment.

FIG. 4 is another diagram illustrating label extraction from a sensor signal according to one embodiment. In some embodiments, the heart rate system downsamples the raw label signals to the frame rate to match the temporal resolution of the features. The resulting downsampled signals are referred to herein as label signals. An example downsampling process is as follows. Each raw label signal is framed with the matching frame length and the frame rate of the feature, i.e., $L_F$ and $R_F$, respectively. For each frame, the label signal equals 1 if more than half of the raw label signal within that frame is 1, and 0 otherwise. FIG. 4 illustrates an example downsampling process. The horizontally-oriented "raw label signal for stage 1" shown at the bottom of FIG. 4 shows one particular raw label signal. The vertically-oriented "label signal for stage 1" is the resultant label signal. The rectangular frames illustrate how the raw label signal is framed.

III. HEARTBEAT DETECTION

In the heartbeat detection step 130, the heart rate system takes the features extracted as input and outputs one or N score signals, which each correspond to a particular heartbeat stage detected, in one embodiment. There are N heartbeat stages per heartbeat cycle, and hence the number of score signals. In an embodiment, each score signal is a series of real numbers between 0 and 1, indicating the probability that each frame belongs to the corresponding heartbeat stage. The nth score signal detects the nth stage of the heartbeat, and thus the heart rate system uses the nth label signal to guide the training. This is an example multi-class classification problem where the number of classes is N.

Long-Short Term Memory (LSTM) and Recurrent Neural Networks (RNN) may be used as classifiers because they can capture and utilize useful temporal structures to achieve frame classification and temporal smoothing at the same time, in some embodiments. A LSTM and RNN are example types of classifiers known to one skilled in the art, which are used to determine which class a sample belongs to by taking a feature vector of the sample as input. Other example types of techniques that may be used include attention mechanisms, pooling, and batch normalization in neural networks. A label signal is the ground truth, which is useful for training.

Figure 5:
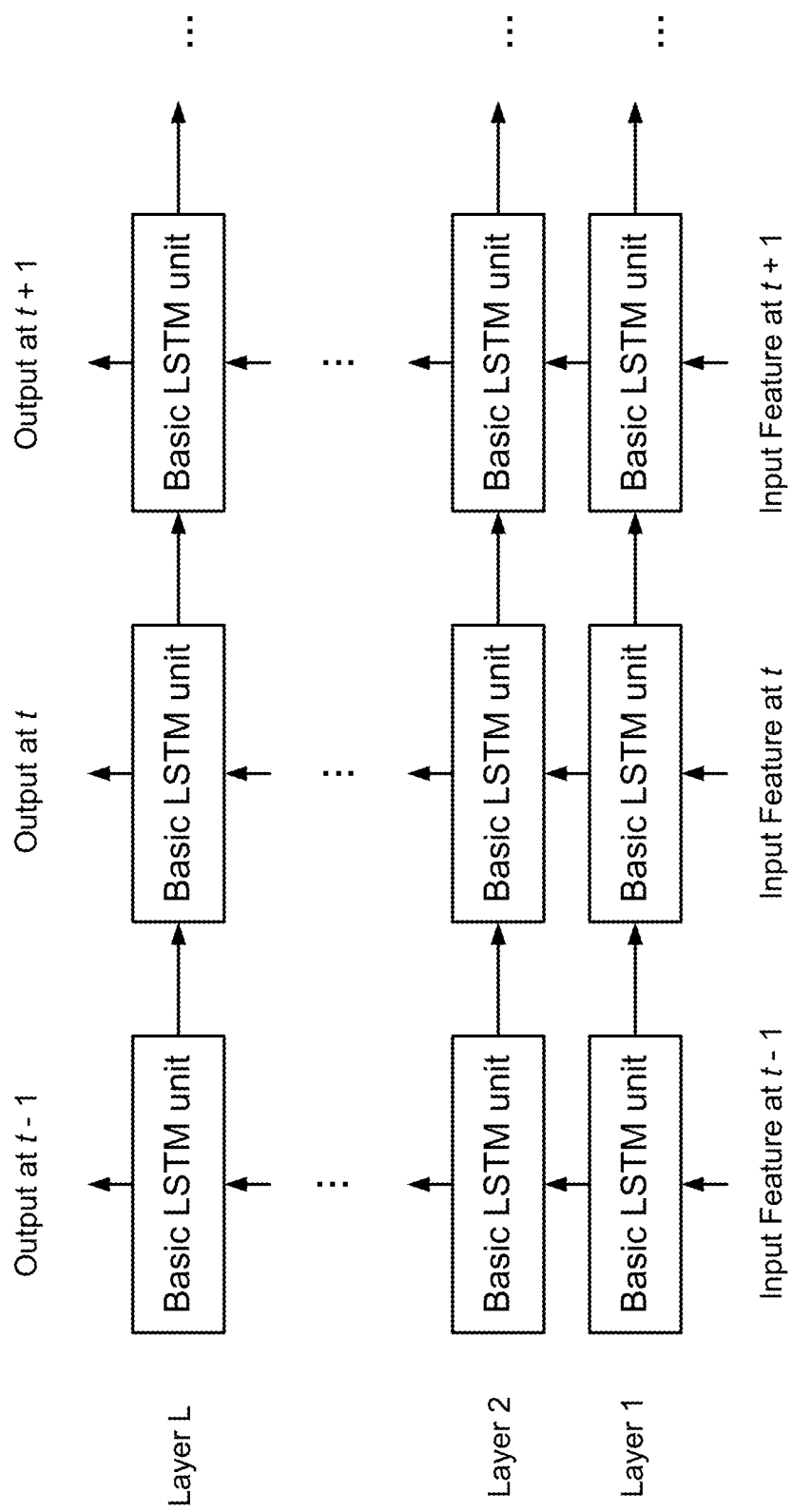
FIG. 5 is a diagram of a classifier according to one embodiment.

FIG. 5 is a diagram of a classifier according to one embodiment. In the embodiment shown in FIG. 5, the LSTM classifier includes a stack of LSTM layers, where the input is fed into the first layer, and the output is the output of the last layer. Each layer is a concatenation LSTM units through time. Each unit takes charge of a single time stamp. Each LSTM unit accepts the information from the past LSTM unit as well as the current input, determines what information to remember from the past and current inputs, and passes the information to its future LSTM unit. A LSTM unit may be parameterized by number of hidden nodes and type of nonlinearity. The LSTM classifier is trained before use. A purpose of training is to find the parameters of the various nodes/edges within and between each LSTM unit using the reference labels and corresponding data by minimizing the loss function, where the loss function measures the distance between the output of the classifier and the reference labels. The parameters may include (or are associated with) weights or biases for the various nodes/edges.

In one embodiment, the heart rate system uses a LSTM or RNN configuration that takes the features described above as input, and outputs an N-dimensional vector (e.g., each output dimension corresponds to a score signal aforementioned) with softmax as output activation function. Softmax is an example function used for neural network modeling discrete distributions. The number of hidden layers and hidden nodes within each layer can be any positive integers. An example value for the number of hidden layers may be 2; an example value for the number hidden nodes in each basic LSTM unit may be 64. An example hidden node activation function applied may be hyperbolic tangent. The output is an N-dimensional vector at each frame, whose dimension n is the nth score signal aforementioned. An example error criterion may be cross entropy.

In other embodiments, the heart rate system may use other types classifiers including, e.g., Vanilla RNN, GRU (Gated Recurrent Unit) RNN, Skip RNN, DilatedRNN, CNN (Convolutional Neural Network), Dialted CNN, Residual Net, as well as their variants by adding or deleting weights and modules. The possible modules that can be added or removed from the aforementioned classifiers include, e.g., dropout, pooling, input normalization, batch normalization, and weight regularization.

The heart rate system may record sensor signals for a number of different scenarios, for example, silence (minimal or no motion), walking, jogging/running etc. Each of these scenarios may correspond to different signal characteristics. To account for these different scenarios, the heart rate system may use a combining or a switching method as described below. The number of scenarios is denoted as K, which may be any positive integer. An example value for K may be 3.

In one embodiment for a combining method, the heart rate system combines and shuffles training features and labels from all different K scenarios. The heart rate system trains a single RNN or LSTM using the combined data.

Figure 6:
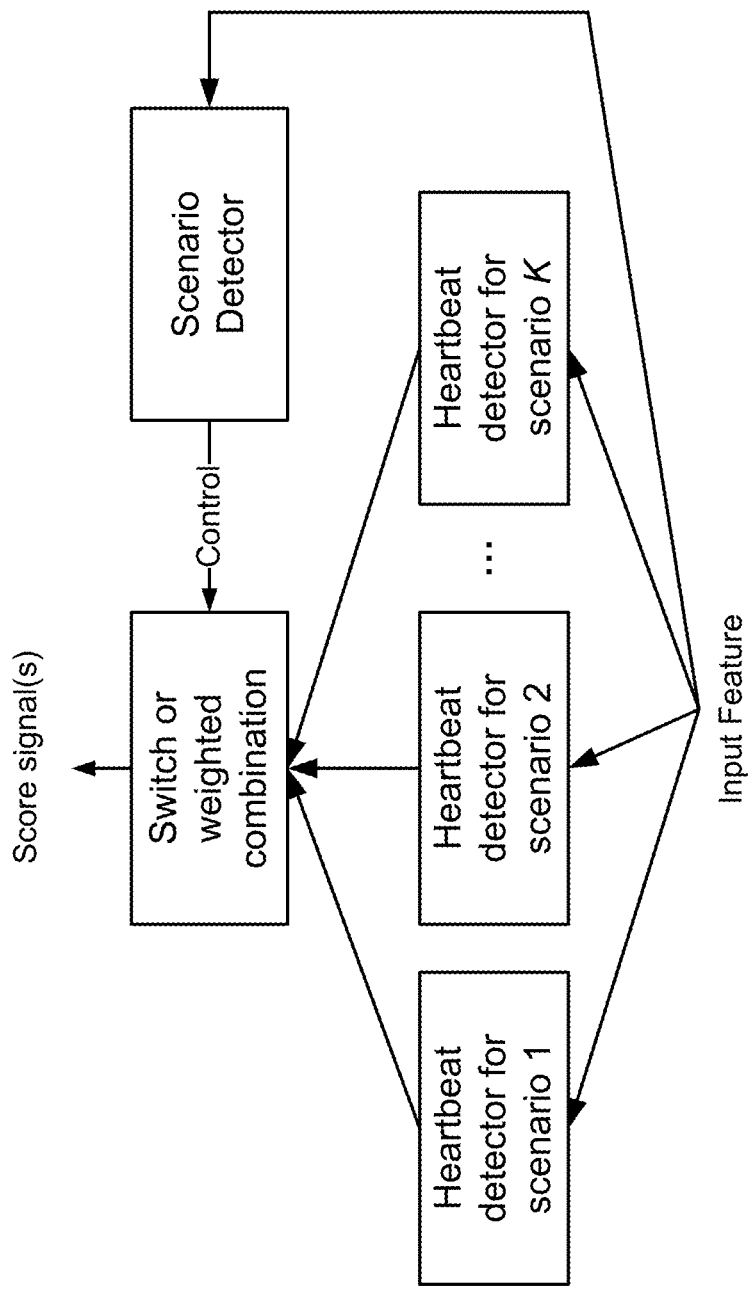
FIG. 6 is a diagram of a process for heartbeat detection using switching according to one embodiment.

FIG. 6 is a diagram of a process for heartbeat detection using switching according to one embodiment. In another embodiment for a switching method, for each of the K scenarios, the heart rate system trains a different detection RNN or LSTM. Thus, there are a total of K detection RNNs or LSTMs. Training data for each scenario may also be manually labeled. Each scenario detection neural network may be of the same architecture as described above.

In some embodiments, the heart rate system selects which detection RNN or LSTM to use based on a scenario classifier. The scenario classifier may be of a similar architecture to each of the detection RNN or LSTM, and take the same input features. However, the output of the scenario classifier may have a dimension K for each frame, instead of N. The kth output represents the probability that the frame is recorded under the kth scenario, where k may be a value from 1 to K. The heart rate system may output a weighted combination of the outputs of the K detection neural networks (e.g., by generating a weighted score); the weights may be based on the K-dimensional output of the scenario classifier.

IV. HEART RATE COMPUTATION

In the heart rate computation step 140, the heart rate system takes in the N score signals as input to generate real-time heart rate estimations, in one embodiment. The heart rate system may use any one of a variety of different methods, for example, using one score signal or using N score signals, which are further described below.

IV. A. Single Score Signal

Figure 7:
FIG. 7 is a diagram of a process for determining heart rate using a score signal according to one embodiment.

FIG. 7 is a diagram of a process for determining heart rate using a score signal according to one embodiment. In an embodiment, the heart rate system selects one score signal. An example choice may be the 1st score signal, though any other score signal may also be selected. The heart rate system may apply a threshold to the selected score signal. The threshold may be pre-determined or adjustable based on other information. The heart rate system determines a heartbeat responsive to determining that the score signal exceeds the threshold. The heart rate system determines a heartbeat period by determining an interval (e.g., of time) between two adjacent heartbeats. The heart rate system may apply a smoothing algorithm to mitigate sudden changes in heartbeat period, e.g., due to missed detection of heartbeats. The heart rate system may also apply an adaptive threshold algorithm to prevent or account for missed heartbeats.

Figure 8A:
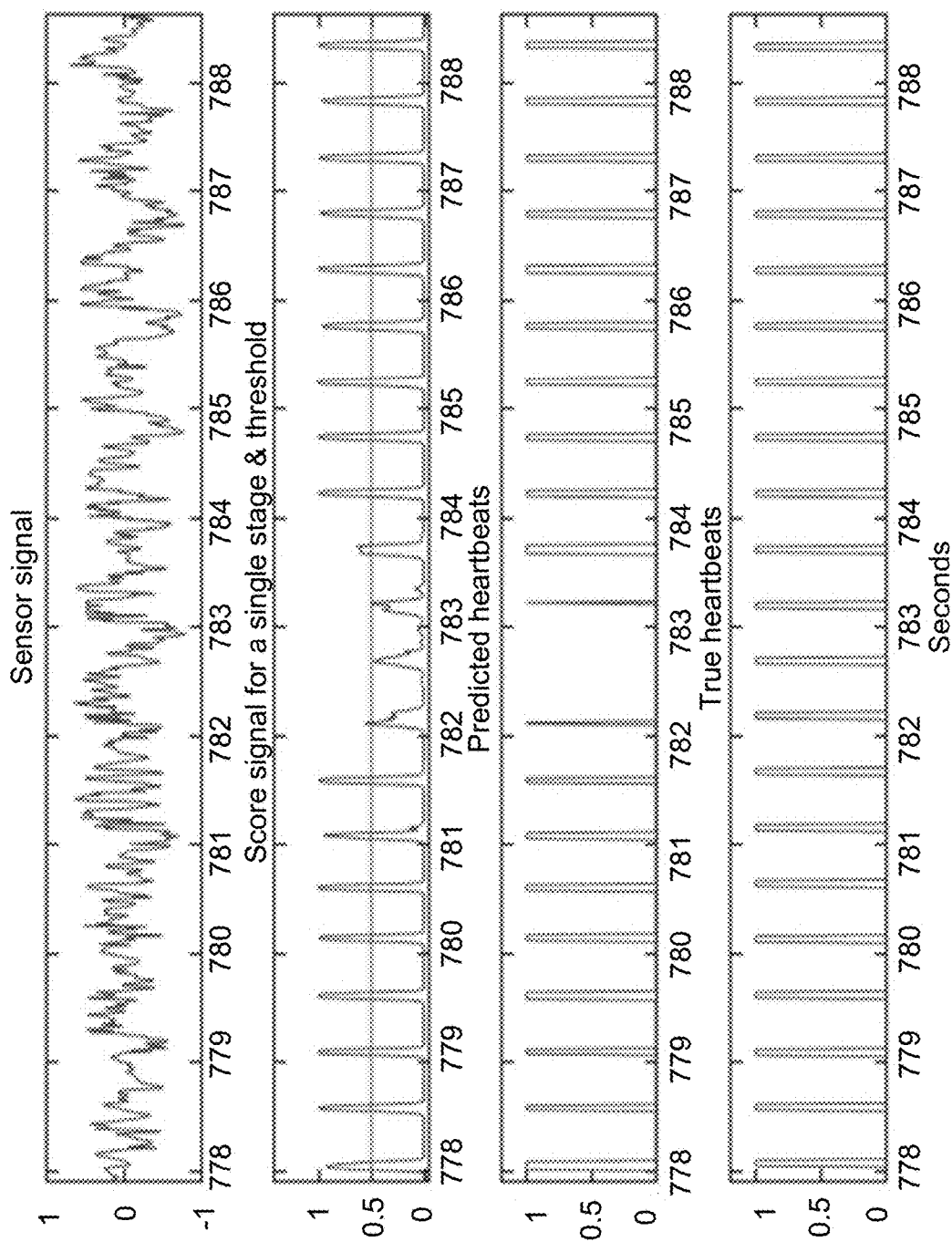
FIG. 8A illustrates signals for heart rate computations using ultrasound sensor data according to one embodiment.
Figure 8B:
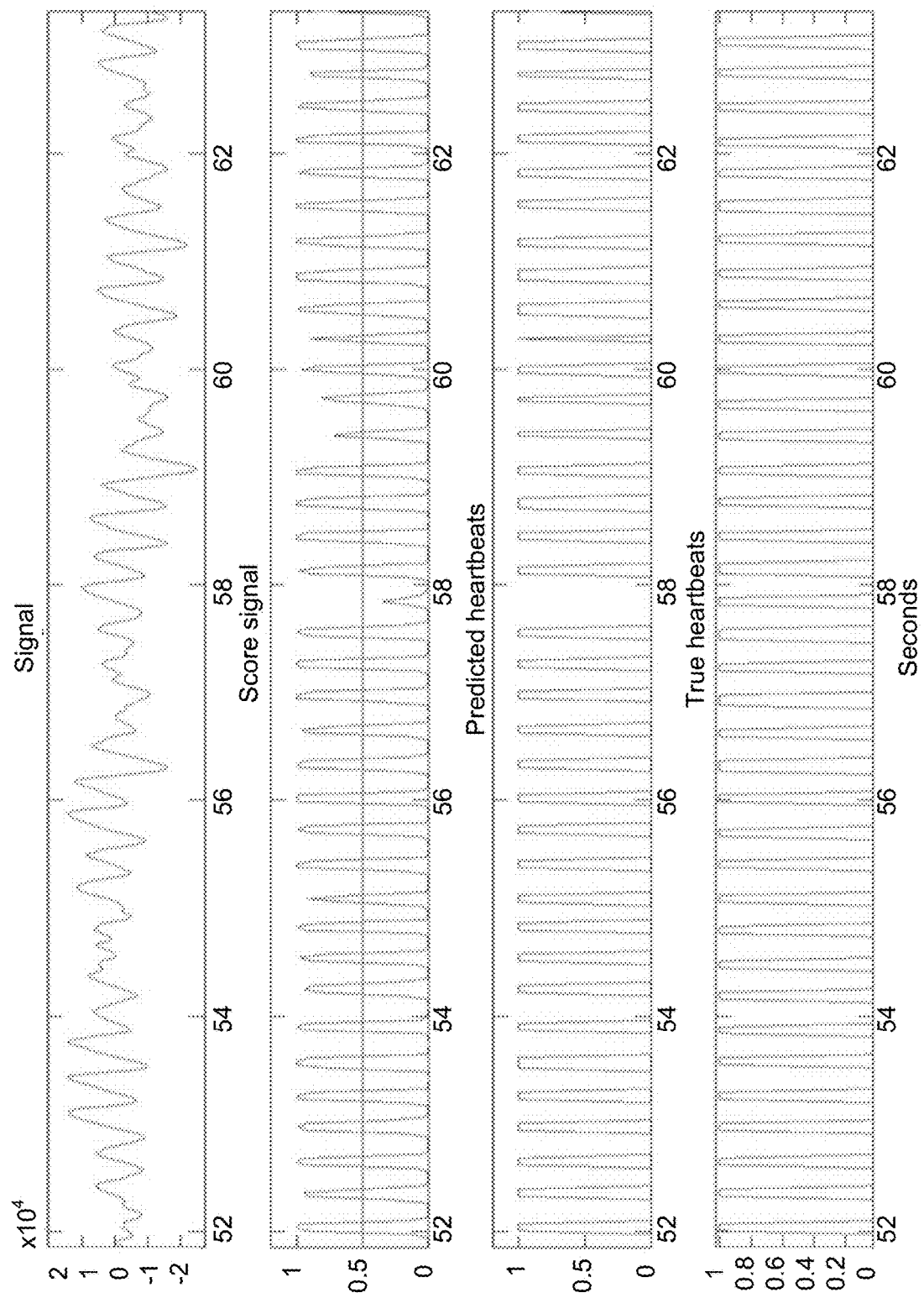
FIG. 8B illustrates signals for heart rate computations using optical sensor data according to one embodiment.

FIG. 8A illustrates signals for heart rate computations using ultrasound sensor data according to one embodiment. FIG. 8B illustrates signals for heart rate computations using optical sensor data according to one embodiment. The example results shown in FIGS. 8A-B may be determined by the heart rate system using the process shown in FIG. 7. Additionally, the ultrasound sensor data may be obtained using the heart rate system 1000 shown in FIG. 10, which is further described below. The optical sensor data may be obtained using the heart rate system 1100 shown in FIG. 11, which is also further described below. The y-axis may represent the amplitude (e.g., in millivolts) of the corresponding signals. The sensor signal shown is a section of real-time heartbeat data sampled from the output of an ultrasound amplifier with the subject performing a running exercise. The score signal represents the output of the classifier. When thumping occurs in running exercise, the heart rate system still detects the heartbeats but occasionally with a lower score. The heart rate system uses a constant threshold (e.g., indicated by the horizontal line at 0.5) to demonstrate an example approach to identify heartbeats. The heart rate system may generate a heart rate determination based on the identified heartbeats, which may be consistent with the true heartbeat data.

IV. B. Multiple Score Signals

Figure 9:
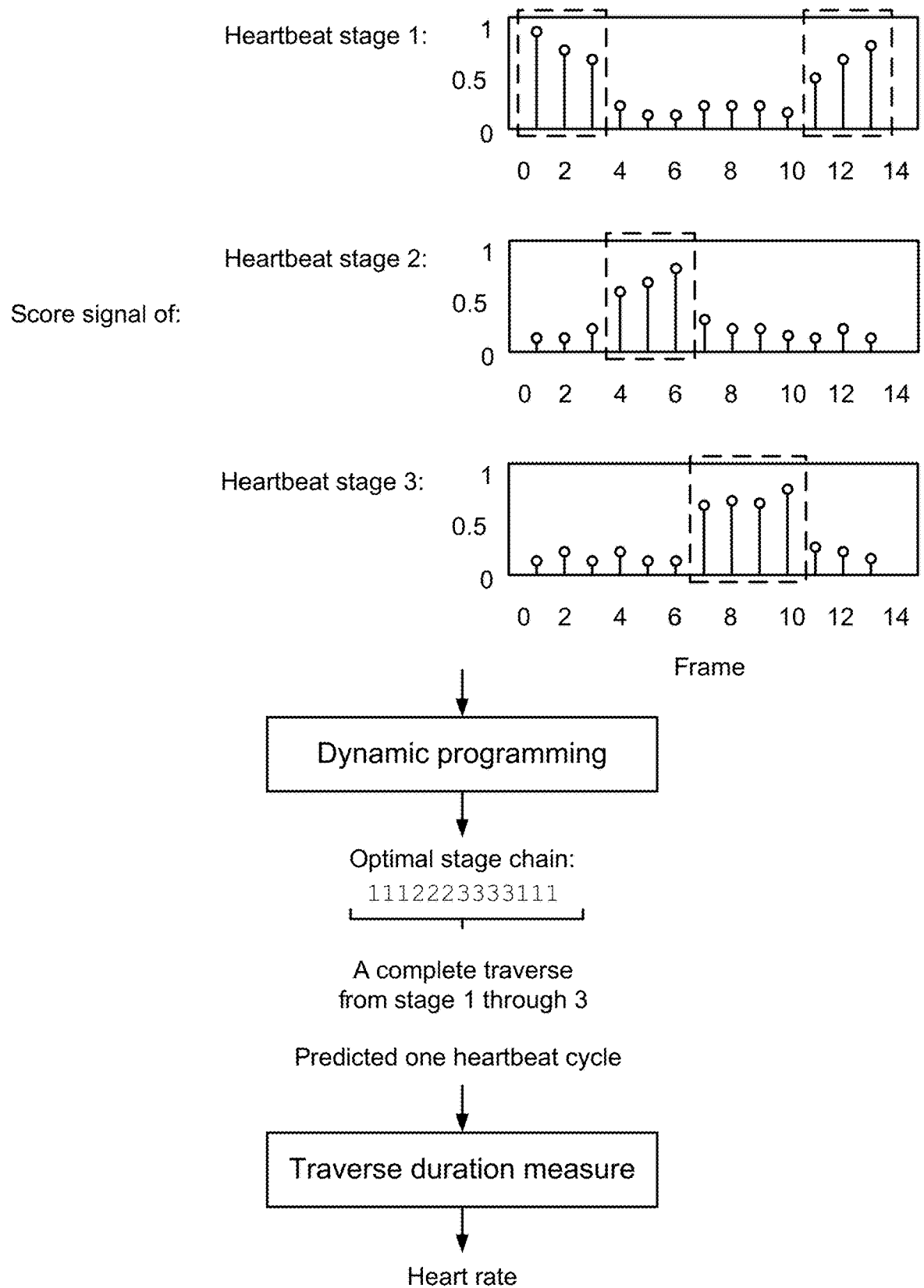
FIG. 9 is a data flow diagram for heart rate computation using score signals of multiple stages according to one embodiment.

FIG. 9 is a data flow diagram for heart rate computation using score signals of multiple stages according to one embodiment. In some embodiments, the heart rate system determines an optimized stage chain using the score signals. In an example, a stage chain is defined as a prediction of which of the N heartbeat stages each frame is in. A heartbeat cycle is completed when the stage chain finishes a one-time sequential traversal from stage 1 to stage N. Therefore, heart rate can be computed by measuring each traverse duration. In the example plots shown in FIG. 9, the heart rate system detects a repeating sequence of heartbeat stage 1, heartbeat stage 2, and heartbeat stage 3, as indicated by the dotted rectangles.

The heart rate system may determine the optimized stage chain using standard dynamic programming algorithms using state chains (e.g., where each state corresponds to a stage of the heartbeat stage chain). For example, the heart rate system uses a dynamic programming algorithm to determine the optimized stage chain (e.g., one stage for each timestamp) that minimizes a target function. The target function may include two parts. One part is state cost, which measures the appropriateness of each stage for each specific timestamp. The other part is transition cost, which penalizes frequent state jump between adjacent timestamps, and can prohibit certain types of state jump.

In an example dynamic algorithm, each timestamp corresponds to a frame. Each state of the algorithm corresponds to a heartbeat stage. The heart rate system determines the state cost using the negative of the N score signals. The transition cost may permit self-transitions, transitions from stage n−1 to stage n, and transitions from stage N to stage 1. The actual values of the transition costs can be determined heuristically or by some estimation schemes.

V. SYSTEM BLOCK DIAGRAMS

The systems described herein can use deep learning algorithms for physical heart rate monitors based on ultrasound sensors, optical sensors/transducers, or other types of sensor technologies. FIG. 10 is a block diagram of a heart rate system 1000 using ultrasound sensors according to one embodiment. FIG. 11 is a block diagram of a heart rate system 1100 including optical sensors according to one embodiment.

For the embodiment shown in FIG. 10, a target location for contact between the heart rate system 1100 and a subject 1050 is the inner side of the wrist of the subject 1050, e.g., either at the Radial artery position or the Ulnar artery position. The ultrasound transducer 1005 may include two piezoelectric (e.g., Lead Zirconate Titanate or PZT) slabs; one PZT slab transmits ultrasound energy to the target and another receives the reflected RF signal that carries the pulsating blood flow information. An ultrasound frequency is provided by the microcontroller 1030 as the Carrier Frequency, which may drive both the ultrasound transducer 1005 and the mixer circuit 1015. At the output of the mixer circuit 1015 is the Doppler signal in audio range that contains the blood flow information, which may be passed through a Butterworth amplifier 1020. The mixer circuit 1015 removes the carrier frequency from the receiver PZT slab.

In some embodiments, the A/D converter 1025 is a high resolution (e.g., up to 24-bit) and high sampling rate (e.g., up to 10 KHz) unit of either Sigma-Delta or Successive Approximation type. The microcontroller 1030 may be a high performance 16-bit or 32-bit chip. External flash memory 1045 may store heart rate determinations. One or more display units 1040 or user interfaces 1035 may vary between different types of devices worn on a wrist of the subject 1050, e.g., watch, sleeve, or wristband.

For the embodiment shown in FIG. 11, a target location for contact between the heart rate system 1100 and a subject 1050 is the center of an outer side of the wrist of the subject 1050. In one embodiment, there are two sets of optical sensor modules (e.g., optical module A 1055 and optical module B 1065), each containing a light-emitting diode (LED) and a photodetector. The wavelength of the light for each module is different; one wavelength is chosen to optimize efficiency in absorption by the red blood cells and the other is chosen for ambient light calibration and compensation purposes. Thus, two input channels in the A/D converter 125 may be required. In some embodiments, the outputs of optical module A 1055 and optical module B 1065 may pass through amplifier A 1060 and amplifier B 1070, respectively, before being input to the A/D converter 1025.

VI. ADDITIONAL CONSIDERATIONS

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for determining a heart rate of a subject, comprising the steps of:
    obtaining temporal sensor data generated by a sensor worn by the subject, the temporal sensor data represented by a plurality of frames of data samples;
    generating, for each frame of the plurality of frames, a feature vector based on a frequency domain representation of the corresponding data samples of the frame;
    inputting the feature vectors to a scenario classifier to determine a scenario of a plurality of scenarios for the temporal sensor data, wherein each of the plurality of scenarios corresponds to a different signal-to-noise level;
    identifying a model from a plurality of trained models according to the determined scenario;
    inputting the feature vectors to the model to generate a series of heartbeat determinations of the subject for each frame of the plurality of frames, wherein the model comprises a first set of parameters and associated weights that represent likelihoods of heartbeats of the subject as a function of time; and
    providing the heart rate of the subject determined based on the series of heartbeat determinations.

2. The method of claim 1, wherein each of the signal-to-noise levels of the plurality of scenarios correspond to a different level of athletic activity of the subject.

3. The method of claim 1, wherein the plurality of scenarios includes at least a first scenario and a second scenario, the first scenario associated with a first set of one or more types of athletic activity and corresponding with a first average signal-to-noise ratio of temporal sensor data, the second scenario associated with a second set of one or more types of athletic activity and corresponding with a second average signal-to-noise ratio of temporal sensor data greater than the first average signal-to-noise ratio.

4. The method of claim 3, wherein the first set of one or more types of athletic activity includes at least one of jogging and running, and wherein the second set of one or more types of athletic activity includes walking.

5. The method of claim 1, wherein the scenario classifier comprises a second set of parameters and associated weights that represent likelihoods of the temporal sensor data corresponding to each of the plurality of scenarios.

6. The method of claim 5, wherein each of the plurality of scenarios is associated with one of a plurality of models including the model, wherein each of the plurality of models comprises a corresponding set of parameters and associated weights that represent likelihoods of heartbeats of the subject as a function of time, and wherein the method further comprises:
    determining the heart rate of the subject by applying the set of weights to outputs of the plurality of models.

7. The method of claim 1, wherein the first set of parameters and associated weights represent likelihoods of heartbeats for each heartbeat stage of a plurality of heartbeat stages, and wherein the model generates the series of heartbeat determinations using a cost function that penalizes transitions between stages of the plurality of heartbeat stages.

8. The method of claim 7, further comprising:
    identifying from the series of heartbeat determinations, one or more transitions between the stages of the plurality of heartbeat stages; and
    determining the heart rate of the subject based at least in part on a duration in time of the one or more transitions.

9. The method of claim 8, wherein the plurality of heartbeat stages includes at least a first heartbeat stage, a second heartbeat stage, and a third heartbeat stage, and wherein the one or more transitions includes (i) a first transition from the first heartbeat stage to the second heartbeat stage and (ii) a second transition from the second heartbeat stage to the third heartbeat stage.

10. The method of claim 9, wherein the duration in time is from a start timestamp of the first heartbeat stage to an end timestamp of the third heartbeat stage.

11. The method of claim 1, wherein the model is trained using feature vectors based on reference signals generated by electrocardiogram sensors worn on subjects, and wherein each of the reference signals is associated with a sensor signal generated by other sensors worn on the subjects simultaneously with the corresponding reference signal.

12. The method of claim 11, wherein the model is trained further using label signals that indicate the presence of heartbeats at timestamps of the reference signals.

13. The method of claim 12, wherein the label signals indicate the presence of heartbeat stages of a plurality of heartbeat stages at the timestamps of the reference signals.

14. The method of claim 11, wherein the electrocardiogram sensors are coupled to a chest strap.

15. The method of claim 11, wherein the other sensors include at least one of an ultrasound sensor, an optical sensor, and a force sensor.

16. The method of claim 1, wherein the sensor worn by the subject is not configured to be worn on a chest of the subject.

17. The method of claim 1, wherein each of the plurality of frames includes at least 256 of the data samples.

18. The method of claim 1, wherein the model is trained using a plurality of tokens including consecutive overlapping subsets of feature vectors.

19. The method of claim 1, wherein the model is a long-short term memory (LSTM) type neural network, includes 2 hidden layers, and includes 64 hidden nodes in each LSTM unit of the model.

20. The method of claim 19, wherein the model uses softmax as an output activation function, and wherein the model uses a hyperbolic tangent as an activation function for the hidden nodes.

21. The method of claim 1, further comprising:
determining one or more heartbeats of the subject not identified by the series of heartbeat determinations by applying at least one of a smoothing algorithm or an adaptive threshold algorithm; and
wherein the heart rate of the subject is determined further based on the one or more heartbeats.

22. The method of claim 1, further comprising:
determining an atrial fibrillation diagnosis for the subject based on the series of heartbeat determinations.

23. The method of claim 1, further comprising:
determining a variability of a plurality of heart rates of the subject based on the series of heartbeat determinations.

24. A computer program product comprising a non-transitory computer readable storage medium having instructions encoded thereon that, when executed by a processor, cause the processor to:
obtain temporal sensor data generated by a sensor worn by a subject, the temporal sensor data represented by a plurality of frames of data samples;
generate, for each frame of the plurality of frames, a feature vector based on a frequency domain representation of the corresponding data samples of the frame;
input the feature vectors to a scenario classifier to determine a scenario of a plurality of scenarios for the temporal sensor data, wherein each of the plurality of scenarios corresponds to a different signal-to-noise level;
identify a model from a plurality of trained models according to the determined scenario;
input the feature vectors to the model to generate a series of heartbeat determinations of the subject for each frame of the plurality of frames, wherein the model comprises a first set of parameters and associated weights that represent likelihoods of heartbeats of the subject as a function of time; and
provide a heart rate of the subject determined based on the series of heartbeat determinations.

25. A system comprising:
a sensor configured to be worn by a subject and generate temporal sensor data represented by a plurality of frames of data samples;
a non-transitory computer readable storage medium having instructions encoded thereon that, when executed by a processor, cause the processor to:
obtain the temporal sensor data from the sensor;
generate, for each frame of the plurality of frames, a feature vector based on a frequency domain representation of the corresponding data samples of the frame;
input the feature vectors to a scenario classifier to determine a scenario of a plurality of scenarios for the temporal sensor data, wherein each of the plurality of scenarios corresponds to a different signal-to-noise level;
identify a model from a plurality of trained models according to the determined scenario;
input the feature vectors to the model to generate a series of heartbeat determinations of the subject for each frame of the plurality of frames, wherein the model comprises a first set of parameters and associated weights that represent likelihoods of heartbeats of the subject as a function of time; and
provide a heart rate of the subject determined based on the series of heartbeat determinations.

* * * * *

UNITED STATES PATENT AND TRADEMARK OFFICE
CERTIFICATE OF CORRECTION

PATENT NO. : 10,709,390 B2
APPLICATION NO. : 15/819763
DATED : July 14, 2020
INVENTOR(S) : Qian et al.

Page 1 of 1

It is certified that error appears in the above-identified patent and that said Letters Patent is hereby corrected as shown below:

On the Title Page

Item (71), Column 1, in "Applicant", Line 1, delete "Mountain View," and insert -- San Mateo, --, therefor.

Signed and Sealed this
Twenty-second Day of December, 2020

Andrei Iancu
*Director of the United States Patent and Trademark Office*